United States Patent
Raisch et al.

(12)

(10) Patent No.: US 6,699,473 B2
(45) Date of Patent: Mar. 2, 2004

(54) HUMAN ANTI-EPIDERMAL GROWTH FACTOR RECEPTOR SINGLE-CHAIN ANTIBODIES

(75) Inventors: Kevin Paul Raisch, Birmingham, AL (US); David T. Curiel, Birmingham, AL (US); James Alan Bonner, Vestavia Hills, AL (US)

(73) Assignee: UAB Research Foundation, Birmingham, AL (US)

( * ) Notice: Subject to any disclaimer, the term of this patent is extended or adjusted under 35 U.S.C. 154(b) by 52 days.

(21) Appl. No.: 09/976,118

(22) Filed: Oct. 12, 2001

(65) Prior Publication Data

US 2002/0058033 A1 May 16, 2002

Related U.S. Application Data

(60) Provisional application No. 60/240,353, filed on Oct. 13, 2000.

(51) Int. Cl.[7] .................. C07K 16/28; A61K 39/395
(52) U.S. Cl. .................. 424/135.1; 424/1.11; 424/1.49; 530/387.1; 530/387.3
(58) Field of Search .................. 530/387.1, 387.3; 424/135.1, 1.11, 1.49

(56) References Cited

PUBLICATIONS

Beerli, et al. Inhibition of Signaling from Type–1 Receptor Tyrosine Kinases Via Intracellular Expression of Single–Chain Antibodies.*Breast Cancer Research and Treatment*, vol. 38, 1996, pp. 11–17.

Mokotoff, et al. Targeting Growth Factor Receptors With Bispecific Molecules. *Current Medical Chemistry*, vol. 3, 1996, pp. 87–100.

*Primary Examiner*—Prema Mertz
(74) *Attorney, Agent, or Firm*—Benjamin Aaron Adler (57) ABSTRACT

Human anti-epidermal growth factor receptor (EGFR) single-chain antibodies (scFvs) were isolated from a human IgM phage display library using purified epidermal growth factor receptor as antigen. Two isolates with different amino acid sequences were identified by ELISA as epidermal growth factor receptor-specific. The scFvs bind to the full length epidermal growth factor receptor and the truncated and/or mutated epidermal growth factor receptor on human cells. These anti-EGFR-scFvs are useful as therapeutic and/or diagnostic agents.

7 Claims, 4 Drawing Sheets

```
Clone        VH→
    ****  **        *     * **    ****  ** *****    ******    CDR1       ****** ***           *    *    **    CDR2    * **
 6   EVQLVESGGGLVQPGGSLRLSCSASGFTFSSYAMHWVRQAPGKGLEYVSAISSNGGSTYYADSVK
63   QVQLVQSGAEVKKPGSSVKVSCKASGGTFSSYAISWVRQAPGQGLEWMGGIIPIFGTANYAQKFQ

**  *** *  *   *       **** ***********   ** *******   *       **      *   **           CDR3        ** *  ****************   VH→
 6   GRFTISRDNSKNTLYLQMSSLRAEDTAVYYCVKD..VGGSSWYWADYFDYWGQGTLVTVSSGSASAP
63   GRVTITADESTSTAYMELSSLRSEDTAVYYCARDPDYYGSGSYYPNWFDPWGQGTLVTVSSGSASAP linker      VL→                                                           CDR1                         
    **************************** *  *    ***********************    ***** *******************
 6   KLEEGEFSEARVQSVLTQPPSLSVSPGQTASITCSGDKLGDKYASWYQQKPGQSPVLVIYQDRKRPSG
63   KLEEGEFSEARVQSALTQPPSVSVSPGQTASITCSGDKLGDKYASWYQLKPAQSPVWVIYQDTKRSSG CDR3                                                   VL→
    *** *****************   *  *  * **********
 6   IPERFSGSNSGNTATLTISGTQAMDEADYYCQAWDSSTPYVFGTGTKVTVLGQPKANPT
63   IPERISGSNSGNTSTLTITGTQAMDEADYYCQAWDSSTAVVFGGGTKLTVLGQPKANPS

*************
 6   VTLFPPSSAAA    (SEQ ID No. 1)
63   VTLFPPSSAAA    (SEQ ID No. 2)
```

HUMAN ANTI-EPIDERMAL GROWTH FACTOR RECEPTOR SINGLE-CHAIN ANTIBODIES

CROSS-REFERENCE TO RELATED APPLICATION

This patent application claims benefit of patent application U.S. Ser. No. 60/240,353, filed Oct. 13, 2000, now abandoned.

BACKGROUND OF THE INVENTION

1. Field of the Invention

The present invention relates generally to the fields of molecular biology and monoclonal antibody technology. More specifically, the present invention relates to human single-chain antibodies that bind specifically to the epidermal growth factor receptor.

2. Description of the Related Art

The epidermal growth factor receptor (EGFR) is a 170 kDa transmembrane glycoprotein consisting of an extracellular ligand binding domain, a transmembrane region and an intracellular domain with tyrosine kinase activity. The binding of growth factors, EGF or TGFα, to the epidermal growth factor receptor results in receptor dimerization, autophosphorylation and induction of a tyrosine kinase cascade, leading ultimately to DNA synthesis and cell division.

The epidermal growth factor receptor gene (c-erb-1), located on chromosome 7, is homologous to the avian erythroblastosis virus oncogene (v-erbB) that induces malignancies in chickens. The v-erbB gene encodes for a truncated protein product that lacks the extracellular ligand binding domain. The tyrosine kinase domain of the epidermal growth factor receptor has been found to have 97% homology to the v-erbB transforming protein.

The epidermal growth factor receptor is overexpressed in a number of malignant human tissues when compared to their normal tissue counterparts. The gene for the receptor is both amplified and overexpressed in a number of cancer cells. Overexpression of the epidermal growth factor receptor is often accompanied by the co-expression of the growth factors, EGF and TGFα, suggesting that an autocrine pathway for control of growth may play a major part in the progression of tumors.

A high incidence of overexpression, amplification, deletion and structural rearrangement of the gene coding for the epidermal growth factor receptor has been found in biopsies of brain tumors. In fact, the amplification of the epidermal growth factor receptor gene in glioblastoma multiforme tumors is one of the most consistent genetic alterations known, with the EGFR being overexpressed in approximately 40% of malignant gliomas. In addition to glioblastomas, abnormal epidermal growth factor receptor expression has also been reported in a number of squamous epidermoid cancers and breast cancers. Many patients with tumors that overexpress the epidermal growth factor receptor have a poorer prognosis than those who do not. Consequently, therapeutic strategies which can potentially inhibit or reduce the aberrant expression of the EGFR are of great interest as potential anti-cancer agents.

Since the advent of hybridoma technology to produce murine monoclonal antibodies (mAbs) developed by Milstein and Köhler in 1975 (1), the therapeutic potential of antibodies is beginning to come to fruition for cancer therapy. There are many reports describing a few antibodies which inhibit cell proliferation of epidermal growth factor receptor-overexpressing cell lines (2–6). One such mouse antibody, mAb 225, was shown to inhibit cell proliferation and block ligand-induced epidermal growth factor receptor tyrosine kinase activity (2–3, 7). Further analysis showed mAb 225 induced a $G_1$ growth arrest and activated an apoptotic pathway after a 24 h exposure to increasing concentrations of antibody (8).

Other monoclonal antibodies which bind to the epidermal growth factor receptor and block ligand binding also show promise for cancer therapy. One group of rat monoclonal antibodies showed a dramatic antitumor effect in xenograft mouse models, with one antibody, ICR62 curing 4 out of 8 mice of the tumor (9). However, the problem with rat and mouse monoclonal antibodies or even the human-mouse chimeric antibody is the possibility of an immune or allergic response with prolonged treatment (10–13).

In order to avoid the human anti-murine antibody (HAMA) response in humans due to the repeated administration of murine mAbs, it is preferable to use human antibody in therapy or diagnostics. A 100% human monoclonal antibody against the epidermal growth factor receptor, E7.6.3, has been shown to completely eradicate human tumor xenografts in mice (4). This antibody is expected to elicit a minimal immune response in humans and shows promise for future cancer therapy. However due to the heterologous vascular structure around the tumor and the molecular size of the antibodies, monoclonal antibodies penetrate the tumor poorly and are unevenly distributed around the tumor.

In order to improve on the use of monoclonal antibodies, intact monoclonal antibodies have been reduced in size to antibody fragments or single-chain antibodies (scFvs). Therefore the development of human anti-EGFR scFvs will enhance its use as a diagnostic and/or therapeutic agent. One advantage of single-chain antibodies is their ability to penetrate deeper into the tumor (14). Thus, these molecules may potentially be more efficacious than intact antibodies for systemic administration. Also single-chain antibodies can be expressed intracellularly (intrabodies) and targeted to a subcellular compartment of the tumor cell or be secreted by the tumor cell and bind in an autocrine/paracrine fashion.

The prior art is deficient in the lack of a 100% human single-chain antibody that binds to the epidermal growth factor receptor. The present invention fulfills this longstanding need and desire in the art.

SUMMARY OF THE INVENTION

The present invention provides a 100% human single-chain antibody (scFv) which binds to the epidermal growth factor receptor. Two single-chain antibodies were isolated from a human IgM phage display library using purified epidermal growth factor receptor as antigen, and identified by ELISA as epidermal growth factor receptor-specific. Sequence analysis confirmed the two isolates as individual clones based on differences in their nucleotide and putative amino acid sequences. One single-chain antibody was shown to bind to the native full length epidermal growth factor receptor and the truncated and/or mutated epidermal growth factor receptor on human cells.

The present invention is directed to a human anti-epidermal growth factor receptor single-chain antibody having a sequence of SEQ ID No. 1 (clone 6) or SEQ ID No. 2 (clone 63), as well as DNA molecules and expression vectors that encode for the expression of the claimed human anti-epidermal growth factor receptor single-chain antibody.

The present invention is also drawn to a pharmaceutical composition comprising the disclosed human anti-epidermal growth factor receptor scFv and a therapeutic and/or diagnostic agent. Preferably, the therapeutic and/or diagnostic agent can be a toxin, a chemotherapeutic agent, a radioisotope, a transition metal or a gene therapy vector.

The present invention is also drawn to a method of treating or imaging a tumor, comprising the step of administering to a patient in need of such treatment or detection an effective amount of a radiolabeled anti-EGFR single-chain Fv of the present invention.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 4 shows the analysis of secretory anti-EGFR-scFv from U87MG cell lines stably transfected with vector (pSECTAG) or anti-EGFR scFv clone 6 (p6.34).

Other and further aspects, features, and advantages of the present invention will be apparent from the following description of the presently preferred embodiments of the invention given for the purpose of disclosure.

DETAILED DESCRIPTION OF THE INVENTION

Because the administration of murine monoclonal antibodies to humans resulted in human anti-murine antibody (HAMA) response, hindering any therapeutic and/or diagnostic potential, the monoclonal antibodies had to be modified. Genetic engineering techniques were used to develop human-murine chimeric monoclonal antibodies. An alternative solution was to develop single-chain antibodies (scFvs). Initially murine scfv were isolated and now technology has progressed to screening naive human phage display libraries for therapeutically and/or diagnostically useful single-chain antibodies of human origin (30–32).

Over the past 10 years, a variety of mouse and human single-chain antibodies have been isolated, including mouse scFvs which bind to the cell surface receptors, epidermal growth factor receptor and erbB-2 (23, 27, 33). Cell proliferation was inhibited when EGFR-overexpressing cell lines were transfected with a plasmid encoding murine anti-EGFR scFvs targeted to the endoplasmic reticulum (ER) or secretory pathway (23, 27). Inhibition of cell proliferation was obtained when erbB-2-overexpressing cell lines were transfected with a plasmid resulting in the production of murine single-chain antibodies which binds the erbB-2 receptor in the ER but no inhibition of cell proliferation was detected with a cytoplasm-targeted scFv (33). Even though both of the single-chain antibodies bound to the extracellular domain of their respective receptor they were expressed as an intracellular scFv (intrabody). The intrabodies were directed to the lumen of the ER to bind the receptor as it was being processed for glycosylation, thereby decreasing the amount of receptor expressed on the plasma membrane and inhibiting cell proliferation. To obtain the greatest antiproliferative effect, the optimal expression and targeting of anti-EGFR single-chain antibodies to the subcellular components involved in epidermal growth factor receptor expression should be undertaken.

The ability of a single-chain antibody to inhibit tumor cell proliferation has considerable potential for cancer gene therapy on its own merit. Moreover, the ability of a scFv to sensitize tumor cells to radiation or chemotherapy treatments will enhance their therapeutic potential. Tumor cells either transfected with scFv expressing plasmid DNA or transduced with viral vectors have shown an increased sensitivity to radiation and/or chemotherapy drugs in vitro and in vivo (34, 35). The anti-erbB-2 scFv, pGT21, was shown to sensitize ovarian cancer cells, SKOV3, to cis-DDP (34). The increased sensitization to cis-DDP was shown to be related to the down-modulation of the erbB-2 protein by targeting the scFv to the ER. The same scFv also sensitized tumor cells to radiation in vitro and in vivo (35). However, a major limitation for these scFvs is the fact that the majority are murine and therefore potentially immunogenic in human.

The present invention discloses a 100% human single-chain antibody (scFv) which binds to the epidermal growth factor receptor. Two scFvs were isolated from a human IgM phage display library using purified epidermal growth factor receptor as antigen, and identified by ELISA as epidermal growth factor receptor-specific. Sequence analysis confirmed the two isolates as individual clones based on differences in their nucleotide and putative amino acid sequences. One scFv was shown to bind to the native full length epidermal growth factor receptor and the truncated and/or mutated epidermal growth factor receptor on human cells.

As used herein, the term "monoclonal antibody" means an antibody composition recognizing a discrete antigen determinant. It is not intended to be limited with regard to the source of the antibody or the manner in which it is made.

As used herein, single chain antibodies or scFvs are polypeptides which consist of the variable (V) region of an antibody heavy chain linked to the V region of an antibody light chain with or without an interconnecting linker. This comprises the entire antigen binding site, and is the minimal antigen binding site. These single-chain antibodies may be produced in bacteria, yeast or eukaryotic cells.

An "antigen-binding site" refers to the part of an immunoglobulin molecule that participates in antigen binding. The antigen binding site is formed by amino acid residues of the N-terminal variable regions of the heavy and light chains. Three highly divergent stretches within the V regions of the heavy and light chains are referred to as "hypervariable regions" which are interposed between more conserved flanking stretches known as "framework regions" or "FRs". In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al., Sequences of proteins of immunological interest, 4th ed., U.S. Dept. Health and Human Services, Public Health Services, Bethesda, Md. (1987).

As an agent by itself, the scFv disclosed herein may inhibit and/or block the growth of epidermal growth factor receptor-expressing human cells. The human anti-epidermal growth factor receptor scFv may also induce apoptosis and cell death in human cells that express epidermal growth factor receptor. A toxin, chemotherapeutic agent, a transition metal or radioisotope generally known in the art can be covalently or non-convalently conjugated to the scFv of the present invention, which would then target the agent to epidermal growth factor receptor-expressing human cells. The scFv disclosed herein may also be used as a part of a bi-specific scFv or some other combination with either itself or another scFv. Furthermore, all or portions of the scFv disclosed herein may be used to target viral or bacterial gene therapy vectors or other agents to bind to epidermal growth factor receptor-expressing human cells. The portions of the scFv could be as small as one complementarity determining region (CDR) or a combination of CDRs from one or both variable regions.

One object of the present invention is to target a scFv to a particular cellular process as a powerful therapeutic technique. Combining the targeted scFv with a gene-based therapeutic approach may enhance the efficacy of single-chain antibodies. The realization of the goals of the current invention will allow for the design of cancer gene therapy treatment using intratumoral injection of a viral vector for successful transduction of a therapeutic scFv to be used in combination with radiation and/or chemotherapy drugs.

A number of methods can be used to deliver the single-chain antibodies of the present invention to tumor cells. In the ex vivo method, the scFv is expressed in bacterial cells (14, 36–37) or eukaryotic cells (24), then isolated and purified prior to administration to the tumor cell lines or tumors implanted in mice. The purified scFv may be administered directly or labeled with a radioisotope, transition metal or toxin prior to administration (38–41). Also, the single-chain antibodies can be engineered to express a bacterial toxin protein on the C-terminal end to enhance the therapeutic potential of the scFv (37). The administration of an ex vivo produced scFv will rapidly localize and penetrate the tumor before being quickly cleared from the circulatory system (14, 38–39).

The in vivo expression of single-chain antibodies can result from transiently or stably transfecting cells with DNA (24–25) or transducing cells with viral vectors. DNA transfer can be accomplished by a variety of standard techniques, such as calcium phosphate, DEAE dextran, electroporation or lipophilic reagents or by using a viral vector to transport the DNA into the cells. Most DNA transfection methods work very well for in vitro experiments; however, viral vectors may be more advantageous for in vivo protocols. Viral vectors commonly used for gene therapy include retrovirus, adenovirus, adeno-associated virus and herpesvirus.

The invention also includes biologically functional fragments of the single-chain antibodies described in this specification. Biologically functional fragments are those fragments sufficient for binding of the antibody fragment to epidermal growth factor receptor. Functional fragments include polypeptides with amino acid sequences substantially the same as the amino acid sequence of the variable or hypervariable regions of the antibodies of the present invention. "Substantially the same" amino acid sequence is defined herein as a sequence with at least 70% percent homology to an amino acid sequence of an antibody of the present invention.

Furthermore, other "substantially homologous" modified antibody polypeptides can be readily designed and manufactured utilizing various recombinant DNA techniques known to those skilled in the art. Modification of the genes may be readily accomplished by a variety of well-known techniques such as site-directed or random mutagenesis. These modifications can include amino acid additions, deletions, substitutions, preferably conservative, and other changes in the sequence of the polypeptide while retaining the appropriate property or biological activity.

Alternatively, polypeptide fragments comprising only a portion of the primary antibody structure and possessing binding and/or effector activities may be produced. Also because, like many genes, the immunoglobulin-related genes contain separate functional regions, each having one or more distinct biological activities, the genes may be fused to functional regions from other genes to produce fusion proteins (e.g. immunotoxins) having novel properties or novel combinations of properties.

The current invention is directed to a human anti-epidermal growth factor receptor single-chain antibody having a sequence of SEQ ID No. 1 (clone 6) or SEQ ID No. 2 (clone 63), as well as DNA molecules and expression vectors that encode for the expression of the claimed human anti-epidermal growth factor receptor scFv.

The present invention is also drawn to a pharmaceutical composition comprising the disclosed human anti-epidermal growth factor receptor scFv and a therapeutic or diagnositic agent. Preferably, the therapeutic or diagnositic agent can be a toxin, a chemotherapeutic agent, a transition metal, a radioisotope or a gene therapy vector.

The following examples are given for the purpose of illustrating various embodiments of the invention and are not meant to limit the present invention in any fashion.

EXAMPLE 1

Isolating EGFR-specific Human Single-chain Antibody (scFv)

Figure 1:
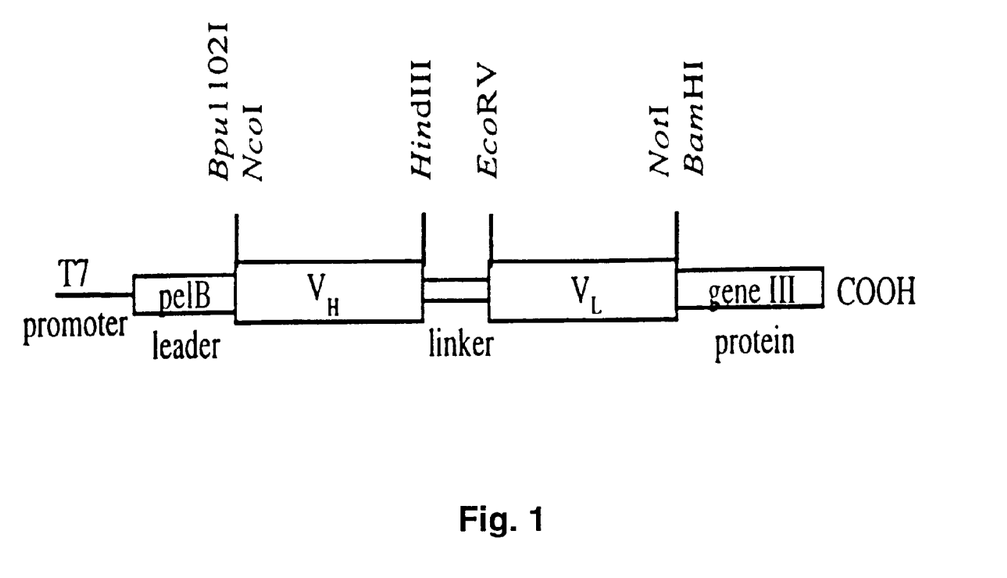
FIG. 1 shows the phagemid, pSEX81, which is optimized for surface expression on the M13 bacteriophage. Depicted here is a single-chain antibody cloned into the multiple cloning site, in-frame with the pelB leader sequence and gene III M13 protein.

In the screening of the phage library for anti-epidermal growth factor receptor scFv, an IgM scFv display library with a calculated complexity of $2 \times 10^7$ independent clones was constructed in pSEX81 (FIG. 1) as described (15) using peripheral leukocyte cDNA prepared from healthy donors. The IgM phage display library was screened for expression of scFvs which specifically bind the EGF receptor (EGFR). The phage library was suspended in 500 ml 2xYT-GA medium (17 g Tryptone, 10 g yeast extract, 100 mM glucose, 100 µg/ml ampicillin and $H_2O$ to 1 liter) to an initial $OD_{600}$ of 0.025. The cells were grown with shaking (240 rpm) at 37° C. until an $OD_{600}$ of 0.1 at which point the cells were superinfected with helper phage, M13K07 (Amersham Pharmacia Biotech), at an MOI of 20. After the addition of helper phage, the cells were mixed gently and left undisturbed for 15 min at 37° C. followed by shaking (240 rpm) for 45 min. The medium was replaced by separating the bacteria at 1500× g for 10 min at room temperature (RT), then the bacterial pellet was suspended in 500 ml 2xYT-AK medium (17 g Tryptone, 10 g yeast extract, 50 µg/ml kanamycin, 100 µg/ml ampicillin and $H_2O$ to 1 liter). The culture was incubated at 37° C. with shaking (240 rpm) for 7 h. The cells were separated from the medium by centrifugation at 6500× g for 15 min at 4° C. The bacteriophage was precipitated out of the supernatant by adding 1/5 volume PEG/NaCl solution (200 g PEG-600, 146.1 g NaCl, up to 1 liter with $H_2O$) and incubating the medium overnight at 4° C.

During the PEG precipitation, affinity purified EGFR (Sigma) in 100 mM sodium carbonate, pH 9.6 was adsorbed to a MaxiSorb Immunotube (Nunc, Rochester, N.Y.) at a concentration of 5–10 µg/ml for 18 h at 4° C. The next day, the immunotube was washed 3 times with PBS, then blocked with 2% skim milk in PBS-T (PBS with 0.05% Tween-20) for 2–3 h at room temperature (the immunotubes were blocked with 0.5% casein-PBS for the second round and 2% skim milk-PBS for the third round). The immunotube was washed 3 times with PBS-T, then stored at 4° C. until ready to use.

The PEG precipitated bacteriophage was separated from the supernatant by high speed centrifugation (10,000× g for 20 min at 4° C.). The pellet was suspended in 4 ml ice-cold phage dilution buffer (10 mM Tris-HCl, pH 7.5, 20 mM NaCl, 2 mM EDTA). The bacteriophage lysate was clarified at 12,000× g for 5 min at 4° C. The supernatant was collected and stored at 4° C. until the colony forming units (cfu) titer was determined.

To determine the cfu titer, an aliquot of the PEG-concentrated bacteriophage was diluted 10-fold up to $10^{-10}$ dilution, then 10 µl of the $10^{-7}$ to $10^{-10}$ dilutions was added to 90 µl of an exponentially growing XL1-Blue culture in LB-tet broth (10 g tryptone, 5 g yeast extract, 0.5 g NaCl, 15 µg/ml tetracycline in 1 liter $H_2O$). The virus was allowed to adsorb for 20–30 min at RT, then mixed with 3 ml of LB-amp (LB broth with 100 µg/ml ampicillin) soft agar (0.5% agar) cooled to 45° C., and immediately overlaid upon an LB-amp agar plate. The plates were inverted and incubated overnight at 37° C. The titer was determined by the number of ampicillin-resistant colonies that have formed at each dilution.

EGFR-specific scFvs were recovered from the phage library by absorbing $10^{11}$ to $10^{12}$ cfu in 4 ml PBS-T to the EGFR-coated immunotubes with rocking for 2 hours at RT. The immunotubes were washed 20 times with PBS-T followed by 20 times with PBS. The EGFR-specific virus was eluted in 1 ml 100 mM triethylamine (Sigma) for 5 min at room temperature, then immediately neutralized with 1 ml 1 M Tris-HCl, pH 7.4 and stored on ice until ready to infect XL1-Blue cells.

To amplify the EGFR-specific scFv bacteriophage, XL1-Blue cells were grown in 20 ml LB-tet broth until an $OD_{600}$ of 0.4. The neutralized-eluted phage was added to the culture, allowed to adsorb undisturbed for 15 min at 37° C., followed by shaking (240 rpm) for 45 min. An aliquot was remove (200 µl) to determine the cfu titer, by making 10-fold dilutions of the 200 µl aliquot in SOB-GA broth (up to $10^{-4}$), then 100 µl from each dilution was spread onto an SOB-GA agar plate (100 mm$^2$) and incubated overnight at 37° C. The cfu titer was determined by counting the number of ampicillin resistant colonies. The remaining cells were separated from the broth by centrifugation at 2000× g for 5 min at RT. The cell pellet was suspended in 1000 µl SOB-GA medium (20 g tryptone, 5 g yeast extract, 0.5 g NaCl, 50 mM $MgSO_4$, 100 mM glucose, 100 µg/ml ampicillin), then spread onto 3 SOB-GA agar plates (150 mm$^2$). After the plates dried, they were inverted and incubated at 37° C. for 18–24 h. The colonies grown on the 150 mm$^2$ plates were removed by scraping the bacteria into 10 ml SOB-GA broth per plate. The bacteria were pooled, then used to inoculate a 250 ml 2xYT-GA broth culture to an $OD_{600}$ of 0.025. Glycerol was added to a concentration of 20% to the remaining bacteria and stored at −80° C. To increase the specificity, the process for isolating EGFR-specific scFvs was repeated 2 additional times.

Putative anti-EGFR-specific scFv clones were isolated from the 2nd round and 3rd round of screening. All clones were stored at −80° C. as a 20% glycerol stock of an overnight broth culture grown in 2x YT-GA broth.

Small Scale Phage Rescue

The scFv bacterial clones were used to inoculate 0.2 ml 2xYT-GA medium and grown overnight at 37° C. Ten µl of the overnight culture was transferred to 1 ml 2xYT-GA medium and incubated with shaking (300 rpm) at 37° C. for 3 hours. M13K07 helper phage ($10^{10}$ cfu) was added to each culture, mixed gently and set undisturbed for 15 min at 37° C., then shaked for 45 min at 300 rpm. The cells were separated by centrifugation at 1000× g for 5 min at room temperature and the supernatant removed, then 1 ml 2xYT-AK medium was added to the cell pellet and incubated with shaking for 7 hours. The cells were removed by centrifugation and the supernatant collected. The supernatant was stored at 4° C. for up to 3 days.

Screening Clones by Phage ELISA

The 96-well MaxiSorb immunoplates (Nunc, Rochester, N.Y.) were coated with 1 µg/ml affinity purified EGFR antigen (Sigma) in 100 mM sodium carbonate, pH 9.6 buffer. The antigen was allowed to adsorb overnight at 4° C., then the antigen was removed and the wells were washed 3 times with PBS-T. The wells were blocked with 2% skim milk-PBS for 2 hours at room temperature. The wells were washed 3 times with PBS-T, then 100 µl of rescued phage was added per well and incubated at room temperature for 2 hours. The wells were washed 3 times with PBS-T, then 100 µl of a 1/1000 dilution of anti-M13-HRP (Stratagene, LaJolla, Calif.) was added to each well and incubated for 1 h at room temperature. The wells were washed 5 times with PBS-T, then 200 µl of the TMB enzyme substrate (Sigma) was added per well. The ELISA plates were incubated at room temperature for 30 minutes, then read at 650 nM. Wells equal to and above $OD_{650}$=0.1 were considered positive and below $OD_{650}$=0.1 were considered negative.

EXAMPLE 2

Sequencing and Analysis of scFv Clones

After 3 rounds of phage panning, individual clones were identified by ELISA as described above. Plasmid DNA was isolated and sequenced according to standard manufacturer's protocol for the ABI DNA sequencer (UAB Automated DNA Sequencing Core Facility). Plasmid DNA was sequenced both directions initially using pelB and gene III primers. Internal sequencing primers were determined from the initial sequence data and synthesized by Operon (Alameda, Calif.). After completion of the scFv sequence, the data was analyzed using SeqWeb software (Genetics Computer Group, Madison, Wis.) for alignment of complementary-determining regions (CDRs) with known variable-chain sequence data.

Figure 2:
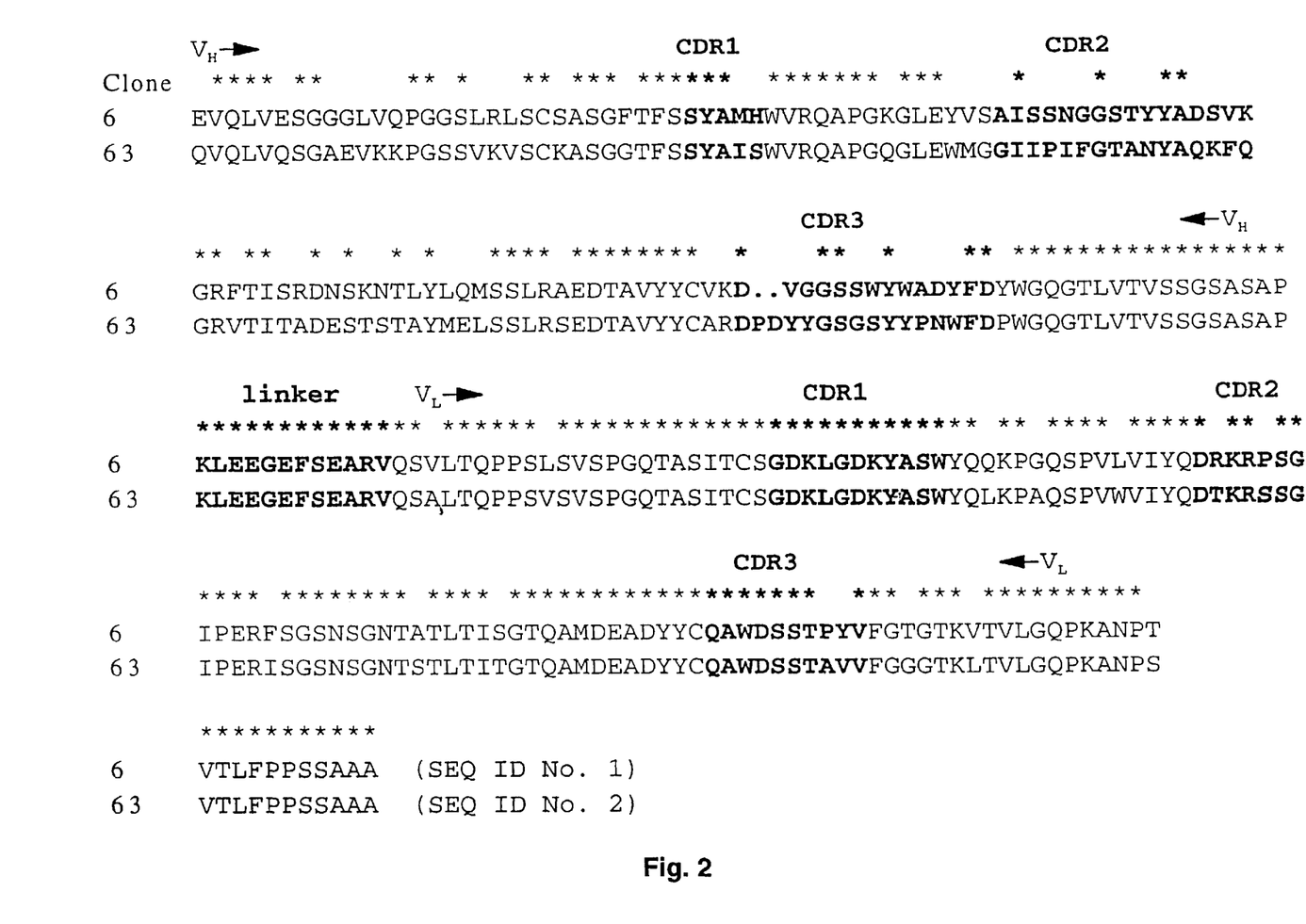
FIG. 2 shows the putative amino acid sequences of anti-EGFR scFv clones pSEX81-6 and pSEX81-63. Clones were sequenced both directions using primers from the pelB leader sequence, the gene III protein and two complementary primers annealing to the alpha tubulin linker sequence. The heavy chain variable region ($V_H$) and light-chain variable region ($V_L$) are identified with their respective CDRs (bold) as described (16). *identifies identical amino acids.

Two clones, pSEX81-6 and pSEX81-63, have been sequenced and their putative amino acid sequences are shown in FIG. 2. The clones are in the order, variable heavy chain ($V_H$)-linker-variable light chain ($V_L$), with both clones containing a lambda $V_L$ chain.

When comparing the two clones, there is a 48% amino acid identity in the $V_H$ chain and an 87% amino acid identity in the $V_L$ chain. The hypervariable or complementarity-determining regions (as defined in ref. 16) are located at the tips of the Fabs in a 3-dimensional structure and have been shown to be primarily involved with antigen binding (17). The CDR1-L region is 100% identical between the two clones, whereas the other CDRs vary from 2 amino acid differences in CDR3-L, CDR2-L and CDR1-H to 10 and 12 amino acid differences in CDR3-H and CDR2-H, respectively. With the high variability between the CDRs of these two clones, each clone may bind to a different antigenic site on the EGFR.

EXAMPLE 3

Targeting the scFv to a Cellular Compartment and Expression of Secretory scFv

In eukaryotic cells, scFvs can be targeted to specific subcellular compartments by engineering the nucleotide sequence to express a protein with the appropriate signal sequences. In this way the scFvs can be modified to be directed to a subcellular compartment where the antibody might prove to be most effective. Recently, Lotti et al. showed that the C-terminal sequence KKXX from the adenovirus E19 protein would enhance the localization of the protein to the cis-golgi complex with some retention in the ER (18). To direct the scFv to the cytoplasm, the hydrophobic amino acid core of the immunoglobulin secretory signal sequence was removed (19). The addition of a nuclear localization signal from the large T-antigen of SV40 virus, PKKKRKV (SEQ ID No. 3), to the N-terminal end can target the scFv to the nucleus (20).

To target mitochondria, the N-terminal presequence of the subunit VIII of human cytochrome coxidase was added to the N-terminal end of the scFv (21). Other investigators have directed scFvs to the lumen of the endoplasmic reticulum by including the endoplasmic reticulum retention signal (SEKDEL, SEQ ID No. 4) at the C-terminus of the polypeptide (22–25). scFvs can also be directed to the secretory pathway by the addition of an immunoglobulin signal peptide on the N-terminal end (23–27).

Figure 3:
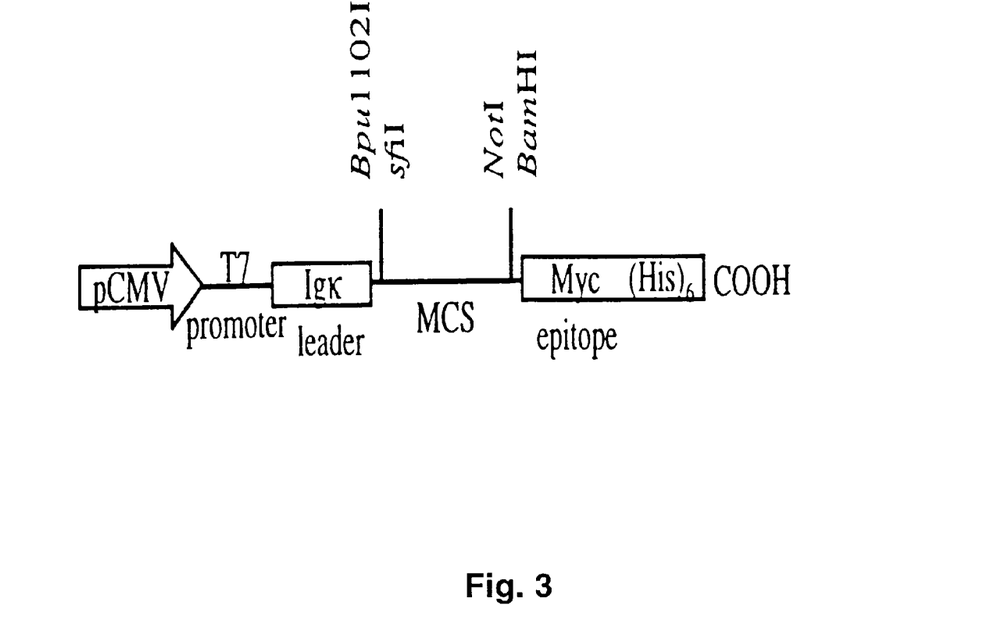
FIG. 3 shows the eukaryotic secreting plasmid, pSECTAG/Bpu/neo which was modified from pSECTAG/Friendly (Invitrogen). The neomycin gene replaced the zeomycin gene and a Bpu 11021 restriction enzyme site was added in-frame with the Ig leader sequence.

In order to express the secretory scFvs in eukaryotic cells, the insert encoding the scFvs must be cloned downstream of an IgK secretory leader sequence in a eukaryotic expression vector. To this end, the eukaryotic expression vector, pSecTag (Invitrogen) was modified at the multiple cloning site to accept the restriction enzyme sites (Bpu1102I and NotI) in the correct orientation and in the proper reading frame between the leader sequence and the myc (mAB 9E10 epitope) and (His)$_6$ tags. Also, the eukaryotic antibiotic resistance gene was changed from zeomycin to neomycin, thus the plasmid is named pSecTag/Bpu/neo (FIG. 3).

Standard cloning techniques were employed to clone the scFv into pSecTag/Bpu/neo. Briefly, 20 ml LB-amp medium were inoculated with XL1-Blue cells expressing the pSEX81-scFv. After an overnight incubation at 37° C., the bacteria were recovered by centrifugation at 4000× g for 5 min. The plasmid DNA were isolated using a Wizard DNA Purification kit (Promega, Madison, Wis.). The pSEX81-scFv plasmid DNA were digested with the restriction enzymes, Bpu1101I and NotI, and separated by agarose gel electrophoresis. The scFv fragment were recovered from the agarose gel using AgarACE Enzyme (Promega). T4 DNA ligase were used to ligate the scFv fragment into the pSecTag/Bpu/neo plasmid which was digested with Bpu1101I and NotI and agarose gel purified. The ligated DNA was use to transform $E.$ $coli$ Top 10F' competent cells (Invitrogen) and plated onto LB-A (LB medium with 100 μg/ml ampicillin) agar plates. After an overnight incubation at 37° C., individual colonies were selected and used to inoculate 5 ml LB-A broth cultures. Plasmid DNA was recovered using the Wizard DNA Purification kit and analyzed for pSecTag/Bpu/neo-scFv by PCR, amplifying the scFv clone between a T7 promoter primer and a myc tag primer. No insert produced a 248 bp PCR product and a positive clone produced a PCR product between 800–1200 bp.

The positive clones were amplified in their bacterial host and the plasmid DNA was recovered using the Wizard PureFection Plasmid DNA Purification System (Promega). The low EGFR expressing human glioma cell line U87MG was transiently transfected with insert positive plasmid DNA or vector alone using the Lipofectin Reagent (Life Technologies). Forty-eight hours after transfection, culture medium was collected and analyzed for secretory scFv to EGFR. Stable transfects were isolated by selecting for antibiotic G-418 resistance with the scFv clones (U87MG-scFv) and vector clones (U87MG-pSecTag/Bpu/neo). The stable transfects were subcultured in 96-well plates at a density of less than 1 cell per well. The culture medium from the confluent wells were screened by ELISA testing for secreted anti-EGFR-scFv. The positive subclones were subcultured in 96-well plates at a density of less than 1 cell per well and the wells grown to confluent monolayers were screened for secreting anti-EGFR-scFv by ELISA. The positive subclones were expanded for further analysis.

EXAMPLE 4

Screening for Anti-EGFR-scFv by Immunoblot and ELISA

One of the stably transfected human glioma sublines, U87MG.6.34.A8 (referred to as clone p6.34) was tested for its ability to secrete a functional, anti-EGFR scFv. The anti-EGFR-scFvs were immunoprecipitated from cell lysates and culture medium. Briefly, the cells were placed on ice, washed three times with ice-cold PBS, lysed in ice-cold lysis buffer (containing 0.025 M Tris-HCl, pH 7.5; 0.25 M NaCl, 0.005 M EDTA, 1% v/v NP-40, 0.001 M phenylmethylsulfonylfluoride, 15 μg/ml aprotinin, 10 μg/ml leupeptin, 0.001 M Na-orthovanadate, 0.05 M Na-fluoride and 0.03 M Na-pyrophosphate) then clarified by centrifugation at 15,000× g for 20 min at 4° C. Protein concentrations were determined using a BCA protein assay kit (Pierce). Equal amounts of protein were immunoprecipitated with mouse anti-myc antibody (9E10 epitope, Stratagene) using Protein A/G beads (Pierce). For immunoprecipitation of secretory scFvs from the culture medium, four-day-old cell culture supernatants were collected from the stably transfected cells. Equal volumes (1 ml) were immunoprecipitated with rat anti-tubulin antibody (Serotec Inc., Raleigh, N.C.) using Protein A/G beads.

Screening for the expression and secretion of the scFvs was by immunoblot, whereby the immunoprecipitated proteins were denatured by boiling in sample buffer (0.125 M Tris-HCl, pH 6.8; 10% glycerol, 1% SDS, 0.7 M β-mercaptoethanol and 0.25% bromophenol blue) for 3 min and separated by SDS-PAGE then transferred to Immobilon-P membrane (Millipore Corp., Bedford, Mass.). Immunoblots were blocked in 10% milk-TBS-T (Tris-buffered saline with 0.05% Tween-20) for 1 hour at room temperature. Primary antibody, mouse anti-myc (Stratagene) was incubated in 2% milk-TBS-T overnight at 4° C. Blots were washed three times in TBS-T followed by incubation with HRP (horseradish peroxidase) labeled secondary antibody, anti-mouse Ig-horseradish peroxidase antibody (Sigma) at room temperature for 1 hour. The blots were washed three times with TBS-T and once with TBS. The blots were developed by chemiluminescence (Amersham Pharmacia Biotech, Piscataway, N.J.).

Figure 4A:
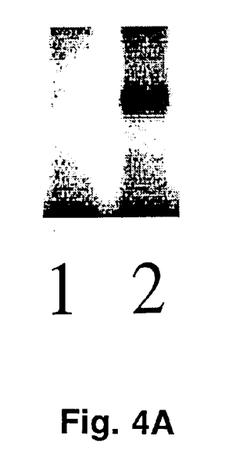
FIG. 4A shows immunoprecipitation of scFv from cell lysates of pSECTAG (lane 1) and p6.34 (lane 2) using anti-myc antibody.
Figure 4B:
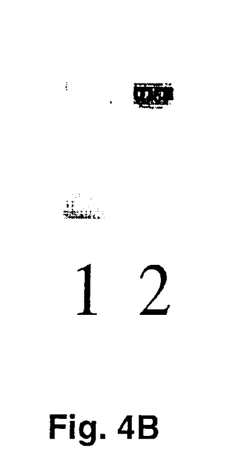
FIG. 4B shows immunoprecipitation of secretory scFv from culture medium of pSECTAG (lane 1) and p6.34 (lane 2) using anti-alpha tubulin antibody. Anti-myc antibody was used to detect scFv for both immunoblots in FIGS. 4A and 4B.

Results show that scFv was immunoprecipitated from the cell lysate (FIG. 4A) and the culture medium (FIG. 4B) of clone p6.34 but not from the control cell line pSECTAG that was stably transfected with the parent vector pSECTAG/Bpu/Neo. These data indicated that scFv was translated and processed into the secretory pathway. However, these data did not indicate whether clone p6.34 scFv binds to the EGFR antigen.

Figure 4C:
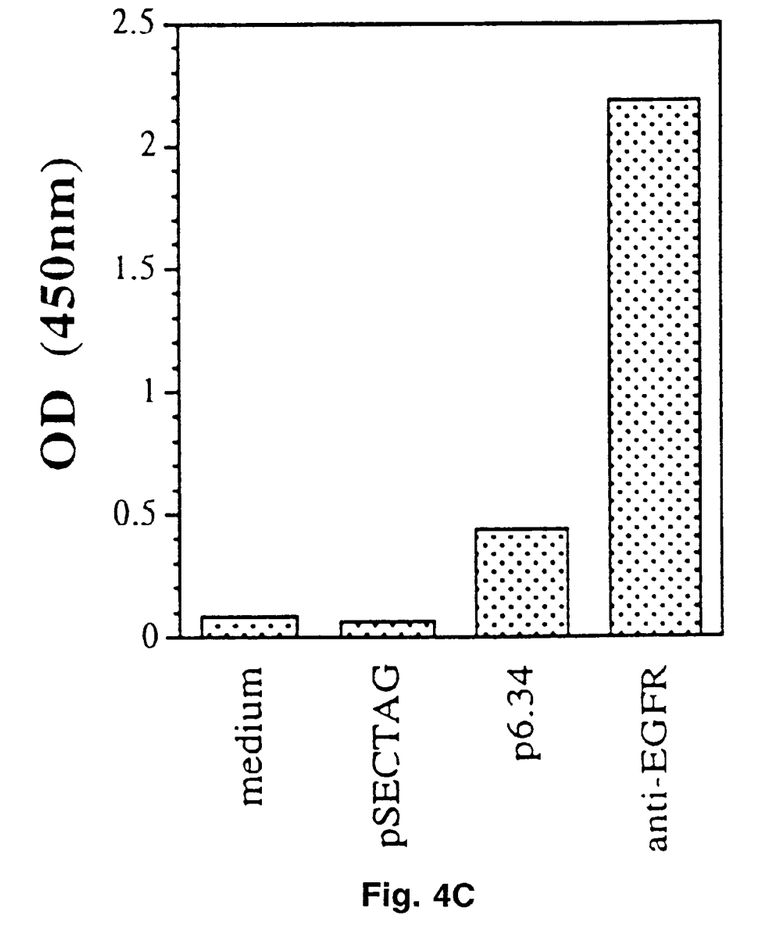
FIG. 4C shows ELISA using cell culture medium, or culture medium from pSECTAG, p6.34 or anti-EGFR mAb (Sigma) to detect binding to the epidermal growth factor receptor antigen. ScFvs were detected using anti-myc-HRP antibody and anti-epidermal growth factor receptor mAb was detected with anti-mouse IgG-HRP antibody and developed with OPD (Sigma).

Therefore, culture medium from stably transfected cells was tested in an ELISA for the expression of secretory scFv against EGFR. The culture medium was clarified by low speed centrifugation (1000× g for 5 min at 4° C.) to remove any cells, then clarified at high speed centrifugation (10,000× g for 15 min at 4° C.) to remove any debris. Cell culture medium (100 μl) was added to each well and incubated for 2h at 37° C. in a $CO_2$ incubator. The wells were washed with PBS-Tween-20 (PBS-T). Secondary antibody, anti-myc (mAb 9E10, Invitrogen) at a 1:1000 dilution in PBS-T was added to each well and incubated for 1 hour at 22° C. After washing the wells, a tertiary antibody, anti-mouse-HRP (Sigma) at 1:2000 dilution in PBS-T was added to each well, then incubated for 1 h at 22° C. The wells were washed and developed with o-phenylenediamine (OPD, Sigma) and read at 450 nm. The results shown in FIG. 4C indicate that clone p6.34 secretes scFv that binds to the purified EGFR antigen.

EXAMPLE 5
Binding of Anti-EGFR-scFv to the Extracellular Domain of EGFR

The ELISA data shown above indicates that clone p6.34 scFv binds to denatured EGFR, however it does not provide any information as to which part of the receptor was recognized by the scFv. The EGFR has three major domains, intracellular, transmembrane and extracellular, any of which may serve as the binding site for clone p6.34. To examine whether the scFv binds to the extracellular portion of the receptor, a FACS analysis was used for this determination. For this assay, culture medium collected from U87MG.pSECTAG or U87MG.pSECTAG.6.34.A8 was allowed to interact with the cell surface of 3 different human glioma sublines; U87MG, U87MG.wtEGFR and U87MG.ΔEGFR (provided by Dr. H-J. Su Huang, UCSD). The U87MG is the parent cell line into which the scFv clones were stably transfected as well as stably transfected with wild-type EGFR (U87MG.wtEGFR) or the truncated EGFR, EGFRvIII (U87MG.ΔEGFR) (28–29). U87MG has a very low number of EGFR, which is one reason why cell proliferation of the stably transfected cell line, clone p6.34, does not appear to be affected by the anti-EGFR scFv (data not shown). The U87MG.wtEGFR subline overexpresses a large number of EGFR/cell (estimated at $>3\times10^6$). The U87MG.ΔEGFR expresses the 135 kdal truncated EGFR which is constitutively phosphorylated (29).

Figure 5:
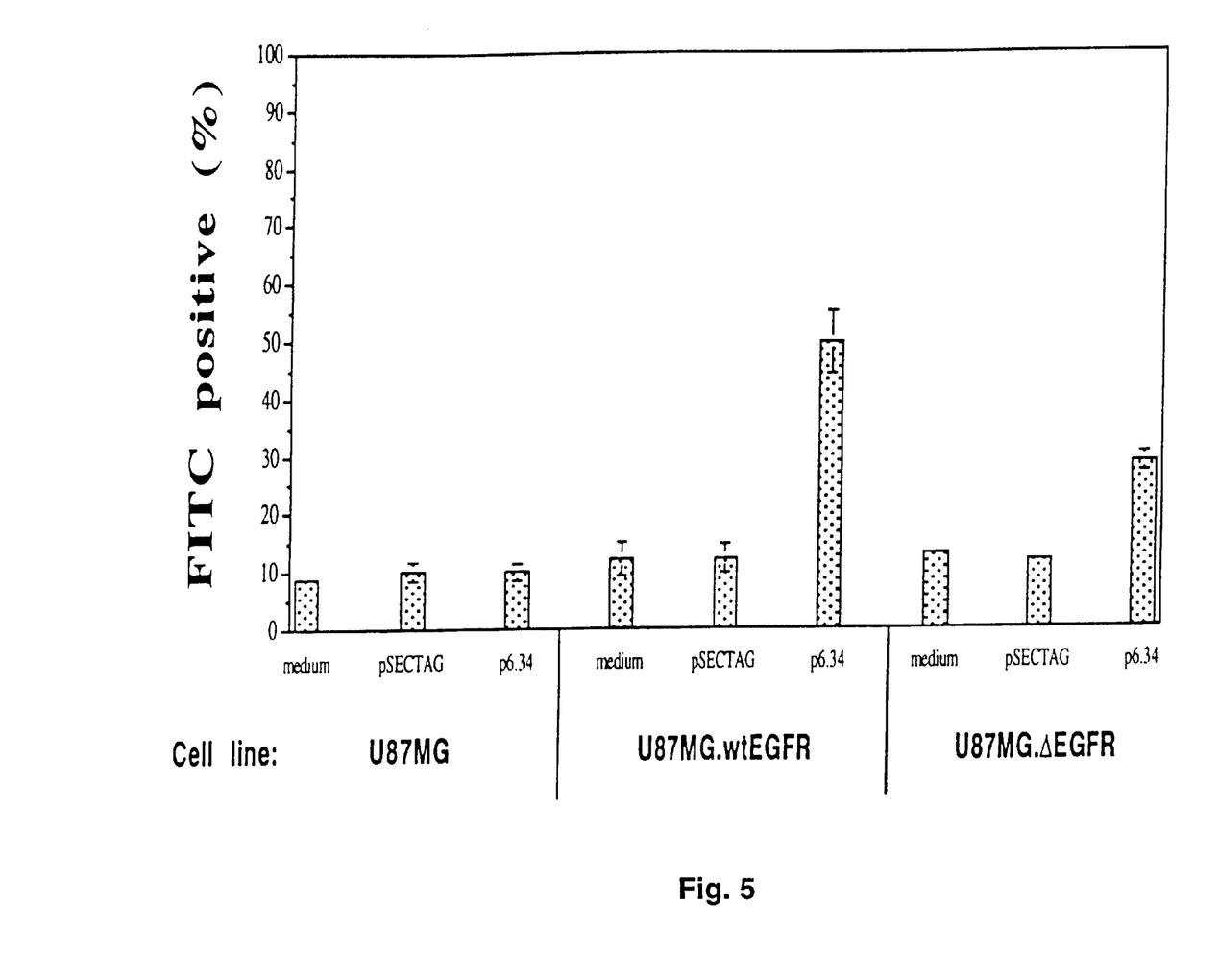
FIG. 5 shows FACS analysis for the detection of anti-epidermal growth factor receptor scFv bound to the extracellular domain of the epidermal growth factor receptor. The cells, U87MG, U87MG.wtEGFR and U87MG.ΔEGFR were incubated with culture medium, culture medium from pSECTAG or p6.34 for 30 min at 4° C. The cells were washed, then incubated with rat anti-alpha tubulin followed by FITC-labeled anti-rat antibody.

The FACS results shown in FIG. 5 indicates that the secretory scFv p6.34 binds to the extracellular domain of U87MG.wtEGFR and U87MG.ΔEGFR. The parent cell line, U87MG, does not have a significant number of receptors on its cell surface which results in no detectable scFv p6.34 binding. The data indicates that clone p6.34 produced a secretory scFv which bound to the cell surface of cells which overexpress EGFR and truncated EGFR (EGFRvIII). Since clone p6.34 bound to a common antigenic site on both prominent forms of cancer-related EGFRs, this scFv might block the surface expression of each receptor when presented in the proper subcellular compartment.

EXAMPLE 6
Radiolabelled Anti-EGFR-scFv for Early Detection of Breast Cancer

Many tumor-specific antigens have been identified as targets for imaging breast cancer. HER-2/neu is overexpressed on 25%–30% of breast cancer cells. The epidermal growth factor receptor, a receptor in the same family as HER-2/neu, has been found to be overexpressed in a high percentage of human carcinomas. A compilation of the literature estimates that approximately 30%–35% of the breast carcinomas have increased levels of epidermal growth factor receptor protein and the increase of epidermal growth factor receptor expression correlates with the loss of estrogen receptor and a poor prognosis.

With the increasing data on the relationship between the overexpression of the epidermal growth factor receptor and poor prognosis, this receptor has become a target for breast cancer imaging. Radiolabelled monoclonal antibodies (mAbs) have been used for imaging epidermal growth factor receptor-overexpressing breast tumors However, due to the heterologous vascular structure around the tumor and the molecular size of the antibodies, the monoclonal antibodies penetrate the tumor poorly and are unevenly distributed around the tumor making imaging more difficult.

In order to improve tumor imaging, intact monoclonal antibodies have been reduced to antibody fragments or single-chain antibodies. The short plasma half-life for the scFv becomes an advantage for tumor imaging because tumor-to-blood ratios are higher than intact monoclonal antibodies and the rapidly eliminated scFv does not accumulate in extravascular spaces and non-target organs. Isotopes used for imaging tumors include $^{111}$In, $^{64}$Cu, $^{131}$I, $^{90}$Y, and $^{99m}$Tc. Technetium-99m is used in the following protocol because the techniques are available for both direct and indirect scFv labelling and $^{99m}$Tc is a low cost, readily available isotope with purely photon radiation, which is widely used in clinical imaging. The 6 h half-life of $^{99m}$Tc is an excellent complement to the scFv which has a rapid clearance from the circulation system allowing for high-contrast imaging.

The radiolabelled scFv of the present invention will be tested for any loss of ability to bind to the epidermal growth factor receptor due to the radiolabelling process. Then, the radiolabelled scFv can be use in mouse xenograft models to determine its ability to bind to large or small xenografts of high, moderate or low epidermal growth factor receptor overexpressing breast cancer cells detected by a gamma camera with computer-enhanced imaging.

Although tissue biodistribution is currently a standard method to assess pharmacokinetics in mice, it suffers from several drawbacks. First, the concentrations of the radiolabelled peptides at each time point are measured from different mice and data are pooled for each separately evaluated group. Second, the number of time points to be sampled are often limited to 3–5 points, consequently, the fast phase of tissue uptake is ignored. Because of the small size of the anti-epidermal growth factor receptor-scFv, the uptake and clearance are expected to be fast in this study. Thus, the pharmacokinetics of the $^{99m}$Tc-scFv will be determined by dynamic imaging using a pinhole gamma camera, and the results are useful for the development of non-invasive imaging method for early detection of breast cancer.

Breast Cancer Cell Lines

The following cell lines are purchased from ATCC (Manassas, Va.): MDA-MB-468, MDA-MB-231 and MCF-7. These cell lines are reported to overexpress EGFR at levels ranging from low (10,000 receptors/cell, MCF-7), medium (100,000 receptors/cell, MDA-MB-23 1) and high (1,000,000 receptors/cell, MDA-MB-468).

Radiolabelling of the Anti-EGFR scFv

The indirect radiolabelling procedure, with the trihydroxamat bifunctional chelating agent trisuccin (42), is used for $^{99m}$Tc labelling of the scFv. The protocol is in two steps consisting of conjugation of trisuccin to the scFv (43), followed by the radiolabelling of the conjugate.

For trisuccin conjugation, the 50 $\mu$l solution of the scFv in DPBS is added to 250 $\mu$L of a 50 mM PBS buffer at pH 8.1. The resulting solution is stirred at 0° C. and the solution of OHA-NHS (5.7 g, 23.5 nmol) in 50 $\mu$l of DMF is added. After 90 min at 0° C., the reaction is quenched by addition of 20 $\mu$l of 2 M glycine in the PBS buffer and the reaction mixture is purified by dialysis against 100 mM acetate buffer, pH 5.5. To this mixture, a solution of trisuccin hydrazide (43) (0.12 mol-1.2 mol) in water (5 $\mu$l -20 $\mu$l) is added. The reaction mixture is stirred at room temperature for 90 min at which time 20 $\mu$l of NaCNBH$_3$ solution in water is added to a final concentration of 100 mM in NaCNBH$_3$. The resulting mixture is stirred gently at room temperature for 18 h followed by purification of the conjugate by size-exclusion HPLC (SEC-HPLC) and eluted with DPBS.

For $^{99m}$Tc-labelling, the procedure reported previously is used (42, 43). Briefly, the $^{99m}$Tc, eluted from a $^{99}$Mo/$^{99m}$Tc generator (Syncor, Birmingham, Ala.) is reduced with a solution of SnCl$_2$ in hydroxyisobutyric acid at room temperature. This solution is added to the trisuccin-scFv and incubated at 35° C. for 30 min. The labelled protein is purified by SEC-HPLC.

Alternately for direct $^{99m}$Tc labelling, cysteine molecules on the purified scFv is radiolabeled with $^{99m}$Tc by previously published methods using a $^{99m}$Tc-D-glucarate transfer method (44, 45). Molecular techniques is used to add a cysteine molecule near the COOH-terminal end of the scFv which will be available for this site directed labelling method. The radiolabelled protein is purified by SEC-HPLC.

Testing the Binding Ability of the Radiolabelled scFv

Whole cells or cell membranes from the three breast cancer cell lines were used in a standard competitive radioimmunoassay to determine if the radiolabelled scFv retains its ability to bind to the EGFR. The radiolabelled scFv used in competition with unlabelled scFv and assays were counted in a gamma counter.

Human Breast Cancer Xenograft Models

Initially, 3 groups of 3 female athymic nude mice, 6 to 8 weeks old, obtained from the National Cancer Institute Frederick Research Laboratory (Frederick, Md.) are injected subcutaneously in the one flank with 2×10$^7$ human breast cancer cells. Each group is injected with one of the three breast cancer cell lines, MDA-MB-468, MDA-MB-231 and MCF-7. When the tumors are approximately 10 mm in diameter, the opposite flank are injected with the same cell line. When the second xenograft is approximately 1 mm in diameter, the mice are injected with the $^{99m}$Tc-scFv and imaged. The xenograft model are repeated 2 additional times and modified if necessary to produce consistent, reproducible results.

In vivo Detection of Breast Cancer Tumors

Planar imaging of mice is performed using Picker Axis gamma camera equipped with a pinhole collimator with 2-mm or 4-mm aperture. The images are acquired with a matrix of 256×256 pixels and a zoom factor of 2. Studies are performed using a 20% energy window, centered on 140 keV photo-peak of $^{99m}$Tc. Mice are imaged immediately after being anesthetized. Previous imaging studies suggest that most mice could be imaged for 45–60 minutes before they recover from the anesthesia. Each mouse receives 50 $\mu$Ci $^{99m}$Tc-scFv IV. Mice are imaged in a prone position a s xenografts are planted subcutaneously in both ventral flanks. A distance of 7.5 cm from pinhole to mice is used for imaging a group of 3 mice simultaneously in one field of view. Dynamic image is performed at 0-1 h, 60 frames of images are acquired at 1 min/frame rate to obtain fast phase for scFv uptake in normal tissue and the tumor. Static images are acquired at 2 h, 4 h, 6 h, respectively. Acquisition time of each image is 20–30 min, which is comparable to that of patient imaging using a gamma camera.

These images are used to determine the optimal imaging time and best tumor to non-tumor image contrast that can be used for future patient imaging. This imaging computerized kinetic model allows one to obtain pharmacokinetics information in same animals and provide direct evidence for the potential of using $^{99m}$Tc-human anti-EGFR-scFv for early detection of breast cancer in patients.

The following references were cited herein:

1. Kohler and Milstein, Nature. 256: 495–7, 1975.
2. Gill et al., Journal of Biological Chemistry. 259: 7755–60, 1984.
3. Sato et al., Molecular Biology & Medicine. 1: 511–29, 1983.
4. Yang et al., Cancer Research. 59: 1236–43, 1999.
5. Modjtahedi et al., British Journal of Cancer. 67: 247–53, 1993.
6. Kawamoto et al., PNAS. 80: 1337–41, 1983.
7. Fong et al., Cancer Research. 52: 5887–92, 1992.
8. Wu et al., Journal of Clinical Investigation. 95: 1897–905, 1995.
9. Modjtahedi et al., British Journal of Cancer. 67: 254–61, 1993.
10. Bruggemann et al., J. Exp. Med. 170: 2153–7, 1989.
11. Khazaeli et al., Journal of Immunotherapy. 15: 42–52, 1994.
12. Co et al., Nature. 351: 501–2, 1991.
13. Baselga et al., Journal of Clinical Oncology. 18: 904–914, 2000.
14. Yokota et al., Cancer Research. 52: 3402–8, 1992.
15. Koch and Dübel, 2000. Generation of antibody libraries from human donors. In: Antibody Engineering. Eds: R. Konterman and S. Dübel. Springer Verlag, Heidelberg/NewYork.

16. Kabat et al., NIH Publication No 91-3242, 1991.
17. Padlan, Molecular Immunology. 31: 169–217, 1994.
18. Lotti et al., Journal of Biological Chemistry. 274: 10413–20, 1999.
19. Biocca et al., Biochem. & Biophysical Res. Comm. 197: 422–7, 1993.
20. Biocca et al., EMBO Journal. 9: 101–8, 1990.
21. Biocca et al., Bio/Technology. 13: 1110–5, 1995.
22. Deshane et al., Gynecologic Oncology. 59: 8–14, 1995.
23. Jannot et al., Oncogene. 13: 275–82, 1996.
24. Jost et al., Journal of Biological Chemistry. 269: 26267–73, 1994.
25. Marasco et al., PNAS. 90: 7889–93, 1993.
26. Dorai et al., Bio/Technology. 12: 890–7, 1994.
27. Beerli et al., Biochem. & Biophysical Res. Comm. 204: 666–72, 1994.
28. Nagane et al., Cancer Research. 56: 5079–86, 1996.
29. Nishikawa et al., PNAS. 91: 7727–31, 1994.
30. Winter et al., Annual Review of Immunology. 12: 433–55, 1994.
31. Marks, et al., Journal of Molecular Biology. 222: 581–97, 1991.
32. Fuchs, et al., Cell Biophysics. 21: 81–91, 1992.
33. Deshane et al., Cancer Gene Therapy. 3: 89–98, 1996.
34. Barnes et al., Clinical Cancer Research. 2: 1089–95, 1996.
35. Stackhouse et al., Intl. J. of Radiation Oncology, Biology, Physics. 42: 817–22, 1998.
36. Colcher et al., J. National Cancer Institute. 82: 1191–7, 1990.
37. Schmidt et al.,. British Journal of Cancer. 75: 1575–84, 1997.
38. Pavlinkova et al., Clinical Cancer Research. 5: 2613–9, 1999.
39. Milenic et al., Cancer Research. 51: 6363–71, 1991.
40. Lorimer et al., PNAS. 93: 14815–20, 1996.
41. Chowdhury et al., PNAS. 95: 669–74, 1998.
42. Safavy et al., Bioconjugate Chemistry, 4: 194–8, 1993.
43. Safavy et al., Bioconjugate Chemistry, 10: 18–23, 1999.
44. Verhaar et al., Journal of Nuclear Medicine, 37: 868–72, 1996.
45. Pak et al., International Journal of Radiation Applications & Instrumentation—Part B, Nuclear Medicine & Biology, 19: 669–77, 1992.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated human anti-epidermal growth factor receptor single-chain antibody having the sequence of SEQ ID NO: 1 or a biologically functional fragment thereof wherein said antibody hinds to the extracellular domain epidermal growth factor receptor.

2. A pharmaceutical composition comprising the anti-epidermal growth factor receptor single-chain antibody of claim 1 and a pharmaceutically acceptable carrier.

3. The pharmaceutical composition of claim 2, further comprising a therapeutic agent.

4. The pharmaceutical composition of claim 3, wherein said therapeutic agent is selected from the group consisting of a toxin, a chemotherapeutic agent, a radioisotope and gene therapy vector.

5. The pharmaceutical composition of claim 2, further comprising a diagnostic agent.

6. The pharmaceutical composition of claim 5, wherein said diagnostic agent is a radioisotope or a transition metals.

7. The anti-epidermal growth factor receptor single-chain antibody of claim 1, wherein said antibody is radiolabeled.

* * * * *

SEQUENCE LISTING

```
<160> NUMBER OF SEQ ID NOS: 2

<210> SEQ ID NO 1
<211> LENGTH: 268
<212> TYPE: PRT
<213> ORGANISM: artificial sequence
<220> FEATURE:
<223> OTHER INFORMATION: amino acid sequence of anti-EGFR scFV
      clone pSEX81-6

<400> SEQUENCE: 1

Glu Val Gln Leu Val Glu Ser Gly Gly Gly Leu Val Gln Pro Gly
                 5                  10                  15

Gly Ser Leu Arg Leu Ser Cys Ser Ala Ser Gly Phe Thr Phe Ser
                20                  25                  30

Ser Tyr Ala Met His Trp Val Arg Gln Ala Pro Gly Lys Gly Leu
                35                  40                  45

Glu Tyr Val Ser Ala Ile Ser Ser Asn Gly Gly Ser Thr Tyr Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Ser Ser Leu Arg Ala Glu Asp
                80                  85                  90

Thr Ala Val Tyr Tyr Cys Val Lys Asp Val Gly Gly Ser Ser Trp
                95                  100                 105

Tyr Trp Ala Asp Tyr Phe Asp Tyr Trp Gly Gln Gly Thr Leu Val
                110                 115                 120

Thr Val Ser Ser Gly Ser Ala Ser Ala Pro Lys Leu Glu Glu Gly
```

```
                        125                 130                 135

Glu Phe Ser Glu Ala Arg Val Gln Ser Val Leu Thr Gln Pro Pro
                140                 145                 150

Ser Leu Ser Val Ser Pro Gly Gln Thr Ala Ser Ile Thr Cys Ser
                155                 160                 165

Gly Asp Lys Leu Gly Asp Lys Tyr Ala Ser Trp Tyr Gln Gln Lys
                170                 175                 180

Pro Gly Gln Ser Pro Val Leu Val Ile Tyr Gln Asp Arg Lys Arg
                185                 190                 195

Pro Ser Gly Ile Pro Glu Arg Phe Ser Gly Ser Asn Ser Gly Asn
                200                 205                 210

Thr Ala Thr Leu Thr Ile Ser Gly Thr Gln Ala Met Asp Glu Ala
                215                 220                 225

Asp Tyr Tyr Cys Gln Ala Trp Asp Ser Ser Thr Pro Tyr Val Phe
                230                 235                 240

Gly Thr Gly Thr Lys Val Thr Val Leu Gly Gln Pro Lys Ala Asn
                245                 250                 255

Pro Thr Val Thr Leu Phe Pro Pro Ser Ser Ala Ala Ala
                260                 265

<210> SEQ ID NO 2
<211> LENGTH: 270
<212> TYPE: PRT
<213> ORGANISM: artificial sequence
<220> FEATURE:
<223> OTHER INFORMATION: amino acid sequence of anti-EGFR scFV
      clone pSEX81-63

<400> SEQUENCE: 2

Gln Val Gln Leu Val Gln Ser Gly Ala Glu Val Lys Lys Pro Gly
                  5                  10                  15

Ser Ser Val Lys Val Ser Cys Lys Ala Ser Gly Gly Thr Phe Ser
                 20                  25                  30

Ser Tyr Ala Ile Ser Trp Val Arg Gln Ala Pro Gly Gln Gly Leu
                 35                  40                  45

Glu Trp Met Gly Gly Ile Ile Pro Ile Phe Gly Thr Ala Asn Tyr
                 50                  55                  60

Ala Gln Lys Phe Gln Gly Arg Val Thr Ile Thr Ala Asp Glu Ser
                 65                  70                  75

Thr Ser Thr Ala Tyr Met Glu Leu Ser Ser Leu Arg Ser Glu Asp
                 80                  85                  90

Thr Ala Val Tyr Tyr Cys Ala Arg Asp Pro Asp Tyr Tyr Gly Ser
                 95                 100                 105

Gly Ser Tyr Tyr Pro Asn Trp Phe Asp Pro Trp Gly Gln Gly Thr
                110                 115                 120

Leu Val Thr Val Ser Ser Gly Ser Ala Ser Ala Pro Lys Leu Glu
                125                 130                 135

Glu Gly Glu Phe Ser Glu Ala Arg Val Gln Ser Ala Leu Thr Gln
                140                 145                 150

Pro Pro Ser Val Ser Val Ser Pro Gly Gln Thr Ala Ser Ile Thr
                155                 160                 165

Cys Ser Gly Asp Lys Leu Gly Asp Lys Tyr Ala Ser Trp Tyr Gln
                170                 175                 180

Leu Lys Pro Ala Gln Ser Pro Val Trp Val Ile Tyr Gln Asp Thr
                185                 190                 195
```

-continued

```
Lys Arg Ser Ser Gly Ile Pro Glu Arg Ile Ser Gly Ser Asn Ser
                200                 205                 210

Gly Asn Thr Ser Thr Leu Thr Ile Thr Gly Thr Gln Ala Met Asp
                215                 220                 225

Glu Ala Asp Tyr Tyr Cys Gln Ala Trp Asp Ser Ser Thr Ala Val
                230                 235                 240

Val Phe Gly Gly Gly Thr Lys Leu Thr Val Leu Gly Gln Pro Lys
                245                 250                 255

Ala Asn Pro Ser Val Thr Leu Phe Pro Pro Ser Ser Ala Ala Ala
                260                 265                 270
```